United States Patent [19]

Malata et al.

[11] Patent Number: 4,626,210
[45] Date of Patent: Dec. 2, 1986

[54] DENTAL HANDPIECE

[75] Inventors: Peter Malata, Bürmoos; Otto Rosenstatter, Seeham, both of Austria

[73] Assignee: Dentalwerk Bürmoos Gesellschaft m.b.H., Bürmoos, Austria

[21] Appl. No.: 717,180
[22] PCT Filed: Jul. 12, 1984
[86] PCT No.: PCT/AT84/00027
§ 371 Date: Mar. 14, 1985
§ 102(e) Date: Mar. 14, 1985
[87] PCT Pub. No.: WO85/00281
PCT Pub. Date: Jan. 31, 1985

[30] Foreign Application Priority Data

Jul. 14, 1983 [AT] Austria .................................. 2583/83

[51] Int. Cl.$^4$ ............................. A61C 1/08; A61C 3/00
[52] U.S. Cl. ........................................ 433/29; 433/126
[58] Field of Search .................................. 433/126, 29

[56] References Cited

U.S. PATENT DOCUMENTS 4,230,453  10/1980  Reimers .................................. 433/29
4,403,956  9/1983   Nakanishi .............................. 433/29
4,403,957  9/1983   Mossie et al. ......................... 433/29

FOREIGN PATENT DOCUMENTS 1412622  4/1972  United Kingdom ................... 433/29

Primary Examiner—Robert Peshock
Attorney, Agent, or Firm—Toren, McGeady, Stanger, Goldberg & Kiel

[57] ABSTRACT

The invention is directed to a dental handpiece 1 comprising a grip sleeve 2 having at least one cordlike light guide 18 in the area of the handpiece head part 4 which passes out of the latter in the direction of the tooth treatment tool 5 and accordingly extends in its entirety within the grip sleeve 2 and is connected at the rear end to a light source 14. In addition, a detachable connecting piece 10 is provided for the connection at the end member 29 of a supply tube for the supply media of the handpiece, the connecting piece 10 being arranged so as to be freely rotatable relative to the grip sleeve 2, wherein the connecting piece 10 is provided with media throughpass ducts 22, 23, 24 which open into it and pass through it and which are connectable with media lines of the grip sleeve 2 leading to the use positions of the handpiece. The invention is characterized in that the light source 14 is arranged in a recess 11 located preferably eccentrically in the grip sleeve 2 and is electrically connected with at least one current conductor 15 which is connectable by means of a contact arrangement 16, 17, 34, 35, known per se, which permits a reciprocal rotation of the grip sleeve and connecting piece 10, with a current conductor 42 which penetrates the connecting piece and has a contact 36 at the end of the connecting piece remote of the tool for connecting to an opposite contact in the supply tube end member 29 (FIG. 1).

6 Claims, 3 Drawing Figures

U.S. Patent     Dec. 2, 1986     4,626,210
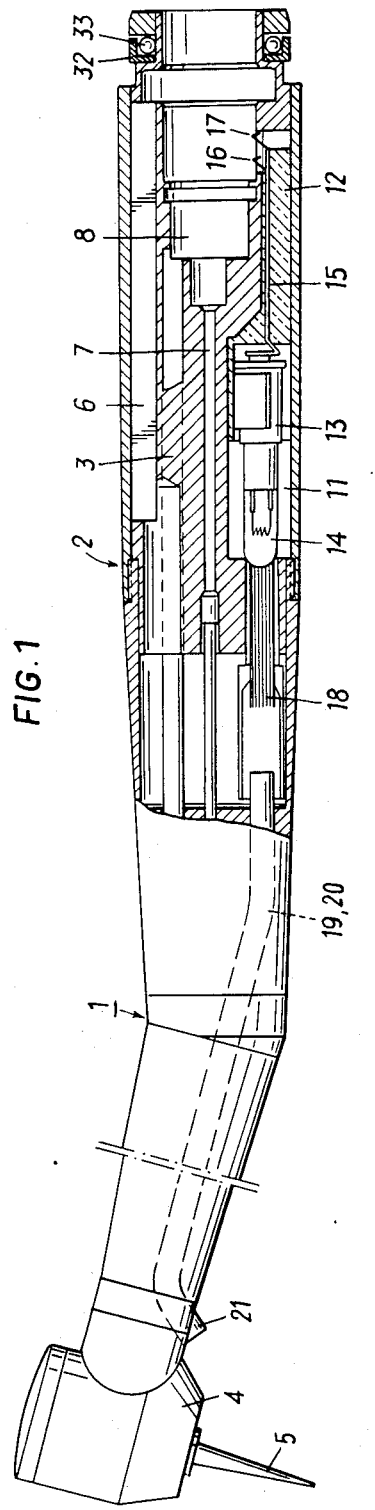
FIG. 1
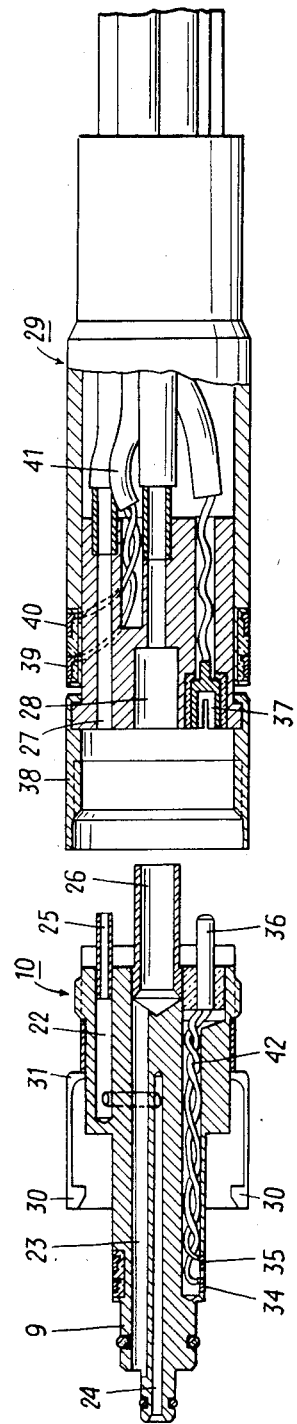
FIG. 3
FIG. 2

DENTAL HANDPIECE

The invention is directed to a dental handpiece comprising a grip sleeve having at least one cordlike light guide in the area of the handpiece head part which passes out of the latter in the direction of the tooth treatment tool and accordingly extends in its entirety within the grip sleeve and is connected at the rear end to a light source and comprising a detachable connecting piece for the connection at the end member of a supply tube for the supply media of the handpiece, the connecting piece being arranged so as to be freely rotatable relative to the grip sleeve, wherein the connecting piece is provided with media throughpass ducts which open into it and pass through it and which are connectable with media lines of the grip sleeve leading to the use positions of the handpiece.

In a known handpiece of this type the light source is centrally located at the front end of the connection piece. Accordingly, the light guide likewise ends centrally at the end of the handpiece remote of the tool so that when the connecting piece is introduced the light source lies opposite the light guide end. Because of this arrangement it is necessary to allow the ducts for the supply media, which ducts are located in the connecting piece, to pass out radially, which necessitates a complicated course of these ducts in the connecting piece, as well as in the grip sleeve.

The object of the invention is to retain the simple course of these ducts, which object is met, according to the invention, in that the light source is arranged in the grip sleeve. The connection of the light source to the current source, which connection thereby becomes necessary, can be effected by means of a contact arrangement, known per se, between the grip sleeve and the connecting piece, which contact arrangement permits the grip sleeve and the connecting piece to rotate freely. The opinion prevailing against the arrangement of the light source in the grip piece is that the sterilization is made more difficult thereby and the light source could be damaged by means of the sterilization. Practical tests prove that this opinion is incorrect.

In addition, a handheld instrument is known in which a transition piece and a lamp chamber, which latter is connectable with the supply tube, are connected at the conventional grip sleeve. Since these parts are rigidly connected with one another, the instrument is heavy and cumbersome, an undesirable effect which is further exacerbated in that the tube is connected at the protracted end of the instrument and therefore, with its weight, brings about a considerable strain on the hand so that it is more difficult to accurately guide the tool at the tooth. The above-mentioned objects of the invention are to be provided without changing the length of the instrument or its weight.

Accordingly, the invention is characterized in a handpiece of the type named in the beginning in that the light source is arranged in a recess located, preferably eccentrically, in the grip sleeve and is electrically connected with at least one current conductor which is connectable by means of a contact arrangement, known per se, which permits a reciprocal rotation of the grip sleeve and connecting piece, with a current conductor which penetrates the connecting piece and has a contact at the end of the connecting piece remote of the tool for connecting to an opposite contact in the supply tube end member.

The invention is directed, in addition, to constructions of the new handpiece.

The subject matter of the invention is shown in the drawing in an exemplary embodiment form. FIG. 1 shows the grip sleeve, including the head part, partly in section; FIG. 2 shows the connecting piece in longitudinal section; and FIG. 3 shows the supply tube end member, likewise partly in section.

The handpiece, designated in its entirety by 1, consists of a two-part grip sleeve 2 and a grip sleeve member 3 located in the latter, as well as a head part 4 having a compressed air-operated drive unit in whose rotor shaft a tool 5 can be inserted. The grip sleeve has several ducts 6, 7 through which the media needed for the drive and cooling are fed to the head part 4. The grip sleeve member is provided with a central, stepped borehole 8 in which a connecting piece 10 provided with a peg 9 can be inserted. In addition, the sleeve member 3 has a recess 11 in which an insulating member 12 is inserted which carries the lamp socket 13 for the light source 14. The insulating member 12 is penetrated by two lines 15 whose ends are made to form contacts 16, 17 which penetrate the wall of the central borehole 8 and project into this borehole in a resilient manner. In addition, a light guide 18 is inserted in the sleeve member 3 whose endface is located opposite the light source 14. It passes into two partial light guides 19, 20 which extend substantially parallel to one another and pass out of the grip sleeve at 21 in the vicinity of the head part 4 and are directed toward the tool 5.

The connecting piece 10 is likewise provided with several ducts 22, 23, 24 for guiding through the drive and cooling media, ducts 22 and 24 being connected with one another by means of a borehole, not shown. These ducts proceed from connecting branches 25, 26 which can be inserted in the supply tube end member 29 with corresponding openings 27, 28. The connecting piece has a bell-shaped sleeve 31 provided with hooks 30, which sleeve 31 is constructed with slots, not shown, so as to be resilient. When the peg 9 of the connecting piece 10 is inserted the hooks 30 slide over a ring 32 which is connected with the grip sleeve 2 by means of a spherical collar 33. In this manner the grip sleeve and connecting piece are freely rotatable relative to one another.

In addition, the peg 9 of the connecting piece 10 has two slip rings 34, 35 which are connected at 42 with two plug pins 36, located one behind the other in FIG. 2, so as to be electrically conducting. These pins 36 engage in resilient sleeves 37 when the supply tube end member 29 is connected with the connecting piece 10 by means of the sleeve nut 38.

When the connecting piece is inserted in the grip sleeve the two slip rings 34, 35 lie in the axial area of the contacts 16, 17 so that a contact arrangement results which does not impair the free rotating ability between the connecting piéce 10 and the grip sleeve 2.

The supply tube end member 29 has two metal rings 39, 40 connected to a control line 41 which leads to a switch for the light circuit. By means of touching the two rings 39, 40 with a finger the switch is actuated in a known manner and the light source is alternately turned on and off.

The invention is not limited to the embodiment example shown. Accordingly, the grip sleeve and connecting piece can consist of electrically conducting material and can serve as current conductor until the supply tube end member. In so doing it is advisable to connect this current conductor to a chassis and ground it, respectively. Then, only one additional current conductor is sufficient in order to dispense with a slip ring and a slide contact. But the construction can also be approached in such a way that the contacts, in this case, are arranged centrically at the front side of the peg 9 of the connecting piece 10 and at the base of the borehole 8, respectively. But a combination of this pair of contacts with a slip ring and slide contact is also possible. In place of the described inductively actuable switch for the light circuit, another switch can be provided in the supply tube end member 29, in the connecting piece 10 or at the grip sleeve 2. But the rings 39, 40 can also be arranged at the connecting member or at the grip sleeve 2, which necessitates a bridging between said parts by means of additional contacts.

In place of a forking of the light guide 18, the latter can extend as a unit until location 21 so that the tool 5 is illuminated only by a light ray.

We claim:

1. Dental handpiece comprising a grip sleeve having at least one cordlike light guide in the area of the handpiece head part which passes out of the latter in the direction of the tooth treatment tool and accordingly extends in its entirety within said grip sleeve and is connected at the rear end to a light source and comprising a detachable connecting piece provided for the connection at the end member of a supply tube for the supply media of said handpiece, said connecting piece being arranged so as to be freely rotatable relative to said grip sleeve, wherein said connecting piece is provided with media throughpass ducts which open into it and pass through it and which are connectable with media lines of said grip sleeve leading to the use positions of said handpiece, characterized in that said light source (14) is arranged in a recess (11) located preferably eccentrically in said grip sleeve (2) and is electrically connected with at least one current conductor (15) which is connectable by means of a contact arrangement (16, 17, 34, 35) which permits a reciprocal rotation of said grip sleeve and said connecting piece (10), with a current conductor (42) which penetrates said connecting piece and has a contact (36) at the end of said connecting piece remote of said tool for connecting to an opposite contact in said supply tube end member (29), wherein said contact arrangement consists of two slip rings (34, 35) and two slide contacts (16, 17).

2. Handpiece according to claim 1, characterized in that said slip rings (34, 35) are provided at said connecting piece (10) and said slide contacts (16, 17) are provided at said grip sleeve (2).

3. Handpiece according to claim 1, characterized in that said grip sleeve (2) and said connecting piece (10) consist of electrically conducting material and form part of the light circuit.

4. Handpiece according to one of claims 1 to 3, characterized in that an inductively acting switch (39, 40) connected to a control line (41) is provided at said grip sleeve.

5. Handpiece according to one of claims 1 to 3, characterized in that an inductively acting switch (39, 40) connected to a control line (41) is provided at said connecting piece (10).

6. Handpiece according to one of claims 1 to 3, characterized in that an inductively acting switch (39, 40) connected to a control line (41) is provided at said supply tube end member (29).

* * * * *